United States Patent [19]
Edelman et al.

[11] Patent Number: 5,794,619
[45] Date of Patent: Aug. 18, 1998

[54] NASAL CANNULA MOUNTED SOLELY BY FRICTIONAL ENGAGEMENT WITH THE COLUMELLA

[76] Inventors: Robert Edelman, 115 Horseshoe Rd., Mill Neck, N.Y. 11765; Louis M. Pagliara, 11 Lowell Rd., Port Washington, N.Y. 11050

[21] Appl. No.: 802,049

[22] Filed: Feb. 18, 1997

[51] Int. Cl.$^6$ .............. A61M 15/08; A61M 16/00; A62B 7/00; A62B 9/00
[52] U.S. Cl. .............. 128/207.18; 128/200.24; 128/912; 128/DIG. 26
[58] Field of Search ............. 128/200.24, 200.26, 128/204.11, 204.12, 206.18, 207.13, 207.18, 912, DIG. 26; 604/94; 606/199, 204.45

[56] References Cited

U.S. PATENT DOCUMENTS

| | | | |
|---|---|---|---|
| 1,256,188 | 2/1918 | Wilson | 606/199 |
| 1,740,083 | 12/1929 | Galvin | 128/204.12 |
| 2,010,485 | 8/1935 | Heath | 606/199 |
| 2,215,188 | 9/1940 | Parks | 128/207.18 |
| 2,569,743 | 10/1951 | Carlock | 606/199 |
| 3,460,533 | 8/1969 | Ríu Plá | 606/199 |
| 4,736,741 | 4/1988 | Payton et al. | 128/207.18 |
| 5,097,827 | 3/1992 | Izumi | 128/204.12 |
| 5,113,857 | 5/1992 | Dickerman et al. | 128/207.18 |
| 5,291,897 | 3/1994 | Gastrin et al. | 128/207.18 |

FOREIGN PATENT DOCUMENTS

| | | | |
|---|---|---|---|
| 174607 | 3/1961 | Sweden | 128/207.18 |

*Primary Examiner*—Kimberly L. Asher
*Attorney, Agent, or Firm*—Myron Amer PC

[57] ABSTRACT

The avoiding of uncomfortable-to-the-touch ear loops and the like in the attaching insertion of oxygen-delivering inserts of a cannula into a patient's nose which uses a 0.25 inch diameter in a circular base of a U-shape of the cannula to provide a chord which in width wise size is smaller than the width wise size of a patient's typical columella which divides in two the nasal cavities, such that the size difference results in a "pinch" fit which holds the cannula in place during its use, and the referred to columella not being sensitive-to-touch thus does not contribute to patient discomfort.

1 Claim, 1 Drawing Sheet

U.S. Patent    Aug. 18, 1998    5,794,619
FIG. 1 PRIOR ART
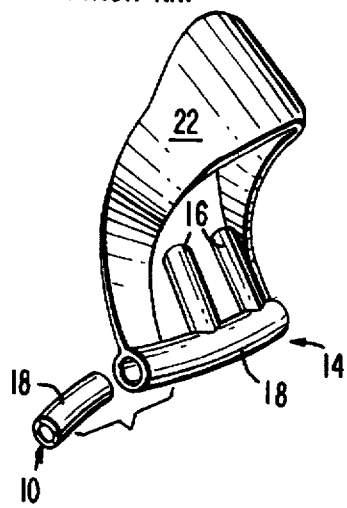
FIG. 2 PRIOR ART
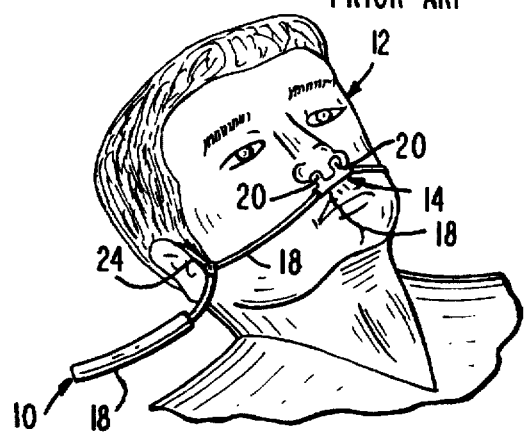
FIG. 3
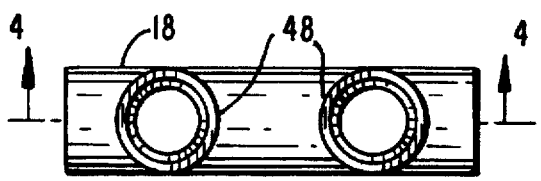
FIG. 6
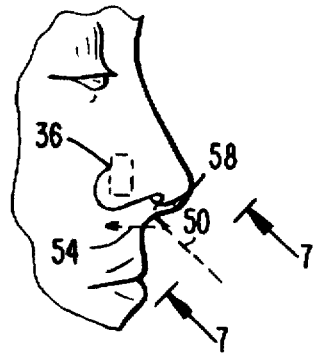
FIG. 4
FIG. 5
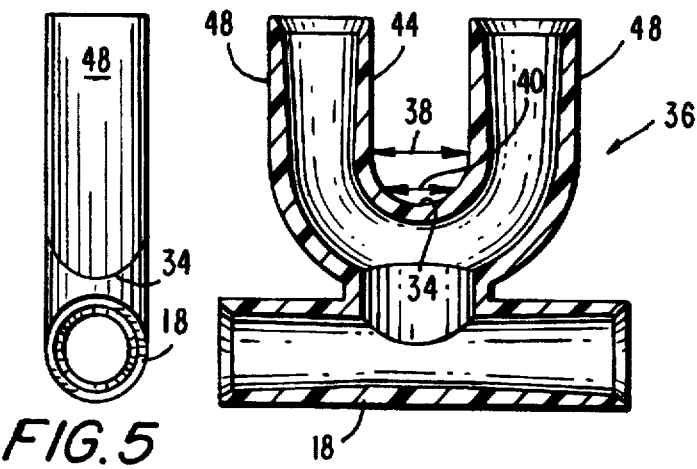
FIG. 7
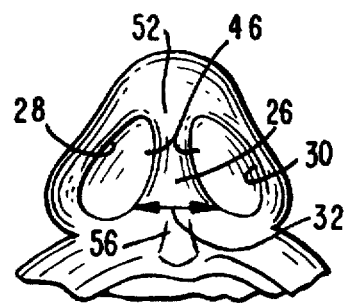

5,794,619

1

NASAL CANNULA MOUNTED SOLELY BY FRICTIONAL ENGAGEMENT WITH THE COLUMELLA

TECHNICAL FIELD

The present invention relates generally to an improved nasal cannula, the improvements more particularly contributing to obviating discomfort in the use of the cannula.

BACKGROUND ART

In delivering oxygen to a hospital patient, the discomfort of the oxygen-supplying tubes of the cannula inserted into the patient's nasal cavities is a circumstance of discomfort which, of course, cannot be avoided. Adding to this, however, are head movements and/or body movements relative to the non-moving or stationary tubing of the cannula which cause inadvertent dislodgement of the inserted tubes, i.e. nasal inserts, of the cannula. In prior patents, to address the problem of inadvertent dislodgement, accessory nose-attaching means are proposed, such as a nose cover in U.S. Pat. No. 3,682,171 for Nasal Cannula issued to Carmelo P. Dali et al. on Aug. 8, 1972, or ear loops in U.S. Pat. No. 4,753,233 for Nasal Cannula issued to Jerry L. Grimes on Jun. 28, 1988, to mention just a few. While effective generally for the limited purposes intended, of obviating dislodgement, the referenced and all other known nose-attaching means increase the discomfort in the use of the cannula because they require in their use contact with sensitive areas of the patient, such as when positioned in encircling relation about and thus in contact with the area behind the patient's ears, and like areas.

DISCLOSURE OF THE INVENTION

Broadly, it is an object of the present invention to provide a comfortable-to-use nasal cannula overcoming the foregoing and other shortcomings of the prior art.

More particularly, it is an object to provide a nasal cannula which is held in place by a friction fit at an attachment site that is not sensitive to touch, thus obviating dislodgement without any attendant discomfort, all as will be better understood as the description proceeds.

BRIEF DESCRIPTION OF THE DRAWINGS

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is a perspective view of a prior art nasal cannula with one form of typical nose-attaching means;

FIG. 2 is similarly a perspective view of a prior art nasal cannula, but with another typical form of nose-attaching means;

FIGS. 3–5 illustrate the within inventive nasal cannula which obviates the need for the use of any additional form of nose-attaching means of the nature exemplified by the means of FIGS. 1 and 2, wherein FIG. 3 is a plan view thereof, FIG. 4 is a cross sectional view as taken along line 4—4 of FIG. 3, and FIG. 5 is a left side elevational view projected from FIG. 4;

FIG. 6 is a perspective view illustrating the within inventive method of applying the cannula of FIGS. 3–5 to a patient's nose; and

2

FIG. 7 illustrates the surface anatomy of the nose illustrated in FIG. 6 as seen in the direction of the arrows 6—6 of FIG. 6.

BEST MODE FOR CARRYING OUT THE INVENTION

As shown in FIGS. 1 and 2, to the end of supplying oxygen from an appropriate source 10 to a patient 12 use is made of a cannula, generally designated 14, having nasal inserts 16 of straight configurations, as best illustrated in FIG. 1 but which will be understood to be also employed on the cannula 14 of FIG. 2, wherein said inserts 16 extend from tubing 18 delivering the oxygen from source 10 into the patient's nasal cavities 20. A well known problem with the prior art cannula 14 is inadvertent dislodgement of the nasal inserts 16 from their projected position within the nasal cavities 20, as might result from head-turning or other movement of the patient 12 relative to the non-moving or substantially stationary tubing 18. To prevent dislodgement, ancillary nose-attaching means are used, such as a nose cover 22 as shown in FIG. 1, or ear loops 24 as shown in FIG. 2. The noted ancillary nose-attaching means 22 and 24 of FIGS. 1 and 2 and all other known means to be used to the same end and purpose contribute to discomfort in the use of the cannula 14 because of contact with sensitive areas of the patient, such as around and behind the ears (FIG. 1) or in covering relation over the nose (FIG. 2) and when positioned within a nasal cavity 20 making contact with the naris, septum or the like (not shown).

Underlying the present invention is the recognition that a patient's columella 26 (FIG. 7) which divides in two the nasal cavities 28 and 30 is of a typical progressively increasing width, from front to rear, and at a rearward or proximal end will be manifested in a width 32 that typically is approximately 5/16 of an inch. This is used to advantage by configurating the base, as at 34, of the within inventive cannula 36 in a circle having a diameter 38 of 0.25 inches which correspondingly will provide a chord 40 at the location illustrated in FIG. 4 which is typically 4/16 of an inch wide, and thus of a smaller dimension than the width dimension 32. As a result of the size differences 32 and 40, the attachment of the cannula 36 to the patient's nose 42 is achieved solely by a friction fit achieved between the cannula wall means 44 bounding the circular configuration 34 which is in inwardly facing relation to opposite outwardly facing sides 46 of the cannula 36 when the columella 26 is in an interposed position between the cannula nasal inserts 48.

As should be readily understood from the preceding description, and as illustrated in FIG. 6, the within inventive method is practiced by initially urging in movement from a clearance position the nasal inserts 48 along an angular ascending movement path 50 until contact is established between the cannula base 34 and the distal end 52 of the columella 26. The cannula 36 is then subsequently urged in movement rearwardly along path 54 until the referenced friction fit is established at the proximal end 56 of the columella 36.

In practice, it has been found that the friction fit resulting from engagement of the wall means 44 at the chord 40 with the columella 26 at the width 32 effectively holds the cannula 36 in place without any need for supporting ear loops 24 or the like or any attaching contact internally of the nasal cavities 58 as might contribute to discomfort in the use of the cannula 36.

While the cannula for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method of supplying oxygen into a nose of a patient having left and right nasal cavities on opposite sides of the columella of the nose of the patient and using a cannula of a type having a U-shaped body, said method comprising the steps of selecting as the sole site of attachment for the cannula the columella of the nose of the patient, using a cannula embodied with a circular configuration in a base of said U-shaped body of a diameter of approximately 0.25 inches, urging said cannula in movement so as to project as nasal inserts length portion extensions of said cannula base initially in angular ascending movement into nasal cavities until contact is established with the columella adjacent a distal end thereof, subsequently urging said cannula in movement rearwardly along the columella until a location along the columella at which a width of the columella is greater than a width of a chord of said circular configuration of said cannula base, and establishing frictional engagement between inwardly facing wall means bounding said circular configuration of said cannula base against outwardly facing sides of the columella, whereby said cannula is held in place solely by said frictional attachment to obviate any need for supporting ear loops and any attaching contact internally of the nasal cavities as might contribute to discomfort in the use of said cannula.

* * * * *